(12) United States Patent
Padua et al.

(10) Patent No.: US 10,953,128 B2
(45) Date of Patent: Mar. 23, 2021

(54) FIBRIN SEALANT PRODUCTS

(71) Applicant: St. Teresa Medical, Inc., Eagan, MN (US)

(72) Inventors: Rudy Padua, Eagan, MN (US); Philip Messina, Eagan, MN (US)

(73) Assignee: St. Teresa Medical, Inc., Eagan, MN (US)

( * ) Notice: Subject to any disclaimer, the term of this patent is extended or adjusted under 35 U.S.C. 154(b) by 22 days.

(21) Appl. No.: 16/176,436

(22) Filed: Oct. 31, 2018

(65) Prior Publication Data

US 2019/0125925 A1    May 2, 2019

Related U.S. Application Data

(60) Provisional application No. 62/580,814, filed on Nov. 2, 2017.

(51) Int. Cl.
| A61L 15/44 | (2006.01) |
| A61L 15/38 | (2006.01) |
| A61L 15/32 | (2006.01) |
| A61L 15/28 | (2006.01) |
| A61L 24/10 | (2006.01) |

(52) U.S. Cl.
CPC .............. *A61L 15/44* (2013.01); *A61L 15/28* (2013.01); *A61L 15/32* (2013.01); *A61L 15/38* (2013.01); *A61L 24/106* (2013.01); *A61L 2300/418* (2013.01); *A61L 2400/04* (2013.01)

(58) Field of Classification Search
CPC ........ A61L 15/44; A61L 24/106; A61L 15/38; A61L 15/32; A61L 15/28; A61L 2400/04; A61L 2300/418
See application file for complete search history.

(56) References Cited

U.S. PATENT DOCUMENTS

| 4,275,721 A | 6/1981 | Olson |
| 4,696,812 A | 9/1987 | Silbering |
| 5,447,423 A | 9/1995 | Fuisz |
| 5,631,011 A | 5/1997 | Wadstrom |
| 5,667,864 A | 9/1997 | Landoll |
| 5,702,715 A | 12/1997 | Nikolaychik |
| 5,773,033 A | 6/1998 | Cochrum |
| 5,795,571 A | 8/1998 | Cederholm-Williams |
| 6,010,627 A | 1/2000 | Hood, III |
| 6,054,122 A | 4/2000 | MacPhee |
| 6,056,970 A | 5/2000 | Greenawalt |
| 6,117,425 A | 9/2000 | MacPhee |
| 6,616,880 B2 | 9/2003 | Thummel |
| 6,753,454 B1 | 6/2004 | Smith |
| 6,762,336 B1 | 7/2004 | MacPhee |
| 6,821,479 B1 | 11/2004 | Smith |
| 7,019,191 B2 | 3/2006 | Looney |
| 7,067,444 B2 | 6/2006 | Luo |
| 7,101,862 B2 | 9/2006 | Cochrum |
| 8,580,532 B2 | 11/2013 | Ikeda |
| 9,399,082 B2 | 7/2016 | Bowlin |
| 9,555,157 B2 | 1/2017 | Olson |
| 2002/0022588 A1 | 2/2002 | Wilkie |
| 2002/0164322 A1 | 11/2002 | Schaufler |
| 2003/0028196 A1 | 2/2003 | Bonutti |
| 2003/0168756 A1 | 9/2003 | Balkus |
| 2004/0018226 A1 | 1/2004 | Wnek |
| 2004/0106617 A1 | 9/2004 | Backstrom |
| 2004/0193088 A1 | 9/2004 | Looney |
| 2004/0229333 A1 | 11/2004 | Bowlin |
| 2005/0186274 A1 | 8/2005 | Kohlrausch |
| 2005/0226916 A1 | 10/2005 | Cochrum |
| 2005/0245966 A1 | 11/2005 | Hammerslag |
| 2005/0284809 A1 | 12/2005 | Looney |
| 2006/0002918 A1 | 1/2006 | Jiang |
| 2006/0013863 A1 | 1/2006 | Shalaby |
| 2006/0141018 A1 | 6/2006 | Cochrum |
| 2006/0155235 A1 | 7/2006 | Sawyer |
| 2006/0204441 A1 | 9/2006 | Atala |
| 2006/0240110 A1 | 10/2006 | Kiick |
| 2006/0264130 A1 | 11/2006 | Karles |
| 2007/0021703 A1 | 1/2007 | McCarthy |
| 2007/0104705 A1 | 5/2007 | Jiang |
| 2007/0160638 A1 | 7/2007 | Mentkow |
| 2007/0160653 A1 | 7/2007 | Fischer |
| 2007/0255238 A1 | 11/2007 | Cochrum |
| 2008/0020015 A1 | 1/2008 | Carpenter |
| 2008/0021545 A1 | 1/2008 | Reneker |
| 2008/0265469 A1 | 10/2008 | Li |
| 2008/0286329 A1 | 11/2008 | Campbell |
| 2009/0053288 A1 | 2/2009 | Eskridge, Jr. |
| 2009/0130186 A1 | 5/2009 | McCarthy |
| 2009/0155342 A1 | 6/2009 | Diegalmann |
| 2009/0177272 A1 | 7/2009 | Abbate |
| 2009/0192214 A1 | 7/2009 | Gravett |
| 2009/0246238 A1 | 10/2009 | Gorman |
| 2009/0291124 A1 | 11/2009 | Bedard |

(Continued)

FOREIGN PATENT DOCUMENTS

| CN | 101214391 A | 7/2008 |
| CN | 102258770 A | 11/2011 |
| CN | 103505758 A | 1/2014 |
| EP | 0693290 A1 | 1/1996 |
| EP | 2441477 A1 | 4/2012 |

(Continued)

OTHER PUBLICATIONS

Stephen W. Rothwell, et al., A Salmon Thrombin-Fibrin Bandage Controls Arterial Bleeding in a Swine Aortotomy Model, The Journal of Trauma, Jul. 1, 2005, pp. 143-149, vol. 59 No. 1.

(Continued)

*Primary Examiner* — Mina Haghighatian
*Assistant Examiner* — Nathan W Schlientz
(74) *Attorney, Agent, or Firm* — Michael A. Bondi; Moss & Barnett

(57) ABSTRACT

A fibrin sealant product having a plurality of layers that each includes a dextran support and at least one fibrin sealant agent. The at least one fibrin sealant agent is placed on the dextran support to form each of the layers. The plurality of layers is placed in a stacked configuration to form the fibrin sealant product. A plurality of crimps is dispersed over a surface of the fibrin sealant product to retain the plurality of layers in a position with respect to each other.

15 Claims, 1 Drawing Sheet

(56) References Cited

U.S. PATENT DOCUMENTS

| | | |
|---|---|---|
| 2010/0016802 A1 | 1/2010 | Tambourgi |
| 2010/0100123 A1 | 4/2010 | Bennett |
| 2010/0158989 A1 | 6/2010 | Mentkow |
| 2010/0209392 A1 | 8/2010 | Sista |
| 2010/0247614 A1 | 9/2010 | Jiang |
| 2010/0254900 A1 | 10/2010 | Campbell |
| 2010/0291182 A1 | 11/2010 | Palasis |
| 2011/0021964 A1 | 1/2011 | Larsen |
| 2011/0034410 A1 | 2/2011 | McCarthy |
| 2011/0071498 A1 | 3/2011 | Hakimimehr |
| 2011/0071499 A1 | 3/2011 | Hakimimehr |
| 2011/0111012 A1 | 5/2011 | Pepper |
| 2011/0112572 A1 | 5/2011 | Miller |
| 2011/0125089 A1 | 5/2011 | Senderoff |
| 2011/0150973 A1 | 6/2011 | Bowlin |
| 2011/0171281 A1 | 7/2011 | Cao |
| 2011/0250257 A1 | 10/2011 | Arthur |
| 2012/0128653 A1 | 5/2012 | Goessl |
| 2012/0184891 A1 | 7/2012 | Johannison |
| 2013/0095165 A1 | 4/2013 | Olson |
| 2013/0095229 A1 | 4/2013 | Olson |
| 2013/0096479 A1 | 4/2013 | Olson |
| 2013/0280321 A1 | 10/2013 | Olson |
| 2013/0287837 A1 | 10/2013 | MacPhee |
| 2014/0023714 A1 | 1/2014 | Gagnieu |
| 2014/0205636 A1 | 7/2014 | Ethicon |
| 2014/0220130 A1 | 8/2014 | Larsen et al. |
| 2015/0017225 A1 | 1/2015 | Hubbell |
| 2015/0258239 A1 | 9/2015 | Lamberti et al. |
| 2016/0193381 A1 | 7/2016 | Olson et al. |

FOREIGN PATENT DOCUMENTS

| | | | |
|---|---|---|---|
| JP | 2000300250 A | | 10/2000 |
| JP | 2005290610 A | | 10/2005 |
| JP | 2007526026 A | | 9/2007 |
| KR | 101318421 B1 | | 10/2013 |
| WO | 1999059647 A1 | | 11/1999 |
| WO | 2000033744 A1 | | 6/2000 |
| WO | 2003/063922 A1 | | 8/2003 |
| WO | 2005062880 A2 | | 7/2005 |
| WO | 2006088912 A2 | | 8/2006 |
| WO | 2006088912 A3 | | 8/2006 |
| WO | 2006090150 A1 | | 8/2006 |
| WO | 20060119487 A2 | | 9/2006 |
| WO | 2006106514 A2 | | 10/2006 |
| WO | 2009042829 A1 | | 4/2009 |
| WO | 2009126870 A2 | | 10/2009 |
| WO | 2010002435 A2 | | 1/2010 |
| WO | 2010002435 A3 | | 1/2010 |
| WO | 2013059346 A1 | | 4/2013 |

OTHER PUBLICATIONS

Jiang et al., Optimization and Characterization of Dextran Membranes Prepared by Electrospinning, Biomacromolecules, 5(2)326-333 (Mar.-Apr. 2004).

Jiang et al., "Modulation of Protein Release from Biodegradable Core-Shell Structured Fibers Prepared by Coaxial Electrospinning", Journal of Biomedical Materials Research Part B: Applied Biomaterials, 79B(1):50-57 (Oct. 2006).

Schanbacher, Anticoagulants and Blood Thinners during Cutaneous Surgery: Always Cometime or Never? Skin Therapy Letter 2004; 9(3).

Kagoma et al., Use of Antifibrinolytic Therapy to Reduce Transfusion in Patients Undergoing Orthopedic Surgery: A Systematic Review of Randomized Trials.

America Family Physician, Cuts, Scrapes and Stitches, Am Fam Physician. Jun. 1, 2004;69(11): 2647-2648.

Bowles et al., Wound Microbiology and Associated Approaches to Wound Management, Clinical Microbiology Reviews, Apr. 2001, p. 244-269.

Sigma-Aldrich, "BIS-TRIS," Specification Comparison, Sigma-Aldrich Co., 2 pages, available at https://www.sigmaaldrich.com/content/dam/sigma-Aldrich/Datasheet/bis-tris_specification_chart.pdf (Year: 2010).

Kumar et al., "Whole Blood Thrombin: Development of a Process for Intra-Operative Production of Human Thrombin," The Journal of the American Society of Extra-Corporeal Technology, vol. 39, No. 1, pp. 18-23 (Year 2007).

Stephen W. Rothwell et al., "The Long Term Immunilogical Response of Swine after Two Exposures to a Salmon Thrombin and Fibrinogen Hemostatic Bandage", Biologicals, vol. 38, No. 6, Nov. 1, 2010, pp. 619-628, XP055178774, ISSN: 1045-1056, DOI: 10.1016/j.biologicals.2010.07.001.

Database WPI Week 201203 Thomson Scientific, London, GB; AN 2011-Q86545 XP002783017 & CN102258770 A (Shanghai Likangrui Biological Eng Co Ltd), Nov. 30, 2011, 2 pgs.

Shaffrey, "Neurosurgical Application of Fibrin Glue: Augmentaton of Dural Closure in 134 Patients", Neurosurgery, vol. 26, Issue 2, 1990, 207-210, 4 pgs.

Ruban, "Management of Incidental Durotomy in Minimally Invasive Spine Surgery", Neurosurgery Focus, 31, (4):E15, 2011, 6 pgs.

Merriam-Webster, "Pledglet", definition, provided by www.merriam-webster.com/dictionary/pledget, pdf captured on Aug. 31, 2018, 3 pgs.

Stephen W. Rothwell et al., "Wound healing and the immune response in swine treated with a hemostatic bandage composed of salmon thrombin and fibrinogen", Journal of Materials Science: Materials in Medicine, Kluwer Academic Publishers, BO, vol. 20, No. 10, May 18, 2009 (May 18, 2009), pp. 2155-2166, X019750141, ISSN: 1573-4838, DOI: 10.1007/S10856-009-3769-2.

International Search Report and Written Opinion for PCT/US2018/058392, 9 pgs.

Stryker Orthopaedics, Triathlon Knee System Surgical Protocol, 2015, 29 pgs.

Lu et al., Perioperative Blood Management Strategies for Total Knee Anthroplasty, Orthopedic Surgery, vol. 10, No. 1, Feb. 2018, 9 pgs.

International Preliminary Report on Patentability received in application No. PCT/US2018/058392, dated May 14, 2020, 7 pgs.

FIBRIN SEALANT PRODUCTS

REFERENCE TO RELATED APPLICATION

This application claims priority to Provisional Applic. No. 62/580,814, filed on Nov. 2, 2017, the contents of which are incorporated herein by reference.

FIELD OF THE INVENTION

The invention generally relates to fibrin sealant products. More particularly, the invention relates to fibrin sealant products that are adapted to be readily customizable.

BACKGROUND OF THE INVENTION

The body's natural response to stem bleeding from a wound is to initiate blood clotting via a complex process known as the coagulation cascade. The cascade involves two pathways that ultimately lead to the production of the enzyme thrombin, which catalyzes the conversion of fibrinogen to fibrin. Fibrin is then cross-linked to form a clot, resulting in hemostasis.

As used herein, the term wound is intended to encompass any type of skin tear, cut or puncture through which blood emanates. The term wound is also intended to encompass tears, cuts and punctures of the dura in the spine through which cerebral spinal fluid flows. The wound may be caused in a variety of situations ranging from combat to surgical operations.

For wounds that are not severe, and in individuals that have no countervening conditions, the body is usually able to carry out this process efficiently in a manner that prevents excessive loss of blood from the wound. However, in the case of severe wounds, or in individuals in whom the clotting mechanism is compromised, this may not be the case.

For such individuals, it is possible to administer components of the coagulation cascade, especially thrombin and fibrinogen, directly to the wound to bring about hemostasis. Bandaging of bleeding wounds is also a usual practice, in part to isolate and protect the wounded area, and also to provide a means to exert pressure on the wound, which can also assist in controlling bleeding.

While these methods may be carried out satisfactorily in cases of mild trauma or under conditions of "controlled" wounding (e.g. surgery), many situations in which such treatments are most needed are also those in which it is the most difficult to provide them. Examples of such wounds include, for example, those inflicted during combat or unanticipated wounds that occur as the result of accidents. In such circumstances, survival of the wounded individual may depend on stopping blood loss from the wound and achieving hemostasis during the first few minutes after injury. Unfortunately, given the circumstances of such injuries, appropriate medical intervention may not be immediately available.

In particular, the treatment of penetrating wounds such as bullet wounds or some wounds from shrapnel is problematic. This is due to the difficulty in placing a hemostatic product and/or therapeutic agents at the actual site of injury, which includes an area that is well below the body surface and difficult or impossible to access using conventional techniques.

Jiang et al. in Biomacromolecules, v. 5, p. 326-333 (2004) teaches electrospun dextran fibers. Agents associated with the fibers (e.g. BSA, lysozyme) are directly electrospun into the fibers. The fibers may also include other polymers electrospun with the dextran.

Jiang et al. in Journal of Biomedical Materials Research Part B: Applied Biomaterials, p. 50-57 (2006) discloses electrospun fibers that are a composite of poly(c-caprolactone) as a shell and dextran as a core. These fibers provide the slow release of agents (bovine serum albumin, BSA) that are also electrospun into the fibers.

Smith et al., U.S. Pat. No. 6,753,454, discloses electrospun fibers comprising a substantially homogeneous mixture of a hydrophilic polymer and a polymer that is at least weakly hydrophobic, which may be used to form a bandage. The bandage may comprise active agents (e.g. dextran). However, the disclosed fibers are not readily soluble in liquid.

MacPhee et al., U.S. Pat. No. 6,762,336, teaches a hemostatic multilayer bandage that comprises a thrombin layer between two fibrinogen layers. The bandage may contain other resorbable materials such as glycolic acid or lactic acid based polymers or copolymers. Neither electrospun fibers nor dextran fibers are taught as components of the bandage.

Smith et al., U.S. Pat. No. 6,821,479, teaches a method of preserving a biological material in a dry protective matrix, the matrix comprising fibers such as electrospun fibers. One component of the fibers may be dextran, but homogeneous dextran fibers are not described.

Cochrum et al., U.S. Pat. No. 7,101,862, teaches hemostatic compositions and methods for controlling bleeding. The compositions comprise a cellulose-containing article (e.g. gauze) to which a polysaccharide is covalently or ionically crosslinked. The crosslinked polysaccharide may be dextran. However, the compositions are not electrospun and exogenous clotting agents are not included in the compositions.

Wnek et al., U.S. Patent Publication No. 2004/0018226, discloses fibers produced by an electroprocessing technique such as electrospinning. The fibers comprise enclosures within the fibers for containing substances that are not miscible with the fibers. Dextran is not taught as a fiber component.

Fisher et al., U.S. Patent Publication No. 2007/0160653, teaches a hemostatic textile comprising hemostatic factors (e.g. thrombin, fibrinogen) but the fibers are formed from electrospun glass plus a secondary fiber (e.g. silk, ceramic, bamboo, jute, rayon, etc.).

Carpenter et al., U.S. Patent Publication No. 2008/0020015, teaches wound dressing comprised of various biodegradable polymers and hydrogels having allogenic or autologous precursor cells (e.g. stem cells) dispersed within the polymers. The polymers may be prepared by electrospinning, and one polymer component may be dextran. However, the polymers cannot be immediately soluble upon contact with liquid, as they must provide a scaffolding for delivery of the cells over time, even though the polymers eventually biodegrade in situ.

Li et al., U.S. Patent Publication No. 2008/0265469, describes electrospun nanofibers that may include dextran. However, the nanofibers are not described as readily soluble in liquids.

Eskridge et al., U.S. Patent Publication No. 2009/0053288, teaches a woven hemostatic fabric comprised of about 65% fiberglass yarn and about 35% bamboo yarn. The fiberglass component may be electrospun, and hemostatic factors such as thrombin may be associated with the fabric, e.g. by soaking the material in a solution of thrombin. This document indicates that dextran may be added as a hygroscopic agent.

There is an ongoing need to provide improved methods and means to initiate blood clotting in wounds to stop or at least slow blood loss. In particular, there is an ongoing need to improve the capability to readily promote hemostasis in severe wounds in a facile manner, especially under circumstances where immediate treatment by medical personnel is limited or unavailable.

Bowlin et al., U.S. Patent Publication No. 2011/0150973, discloses a method of delivering one or more agents of interest to a location of interest. The method includes applying or delivering to a location of interest a hemostatic product. The hemostatic product includes electrospun dextran fibers that dissolve upon contact with liquid. The hemostatic product also includes one or more agents of interest associated with said electrospun dextran fibers. Applying or delivering results in dissolution of the electrospun dextran fibers in liquid at the location of interest to thereby release the one or more agents of interest into the liquid.

Olson, U.S. Patent Publication No. 2016/0038627, describes a method in which a cutter that cuts the hemostatic products into a desired size causes the hemostatic layers to resist separation. This process also causes the hemostatic agents to be retained in the hemostatic products.

SUMMARY OF THE INVENTION

An embodiment of the invention is directed to a fibrin sealant product having a plurality of layers that each include a dextran support and at least one fibrin sealant agent placed on the dextran support. The plurality of layers is placed in a stacked configuration to form the fibrin sealant product. The plurality of crimps is dispersed over a surface of the fibrin sealant product to retain the plurality of layers in a position with respect to each other.

Another embodiment of the invention is directed to a method of preparing a fibrin sealant product. A plurality of layers is fabricated by forming a dextran support and dispensing at least one fibrin sealant agent on the dextran support. The layers are arranged in a stacked configuration to form the fibrin sealant product. A plurality of crimps is applied to the fibrin sealant product to retain the plurality of layers in a stationary position with respect to each other. The plurality of crimps is dispersed over a surface of the fibrin sealant product.

Another embodiment of the invention is directed to a method of preparing a fibrin sealant product. A plurality of layers is fabricated by forming a dextran support and dispensing at least one fibrin sealant agent on the dextran support. The layers are arranged in a stacked configuration to form the fibrin sealant product. A plurality of crimps is applied to the fibrin sealant product. The plurality of crimps is dispersed over a surface of the fibrin sealant product. The fibrin sealant product is cut to change at least one of a shape and a size of the fibrin sealant product. The plurality of crimps retains the plurality of layers in position with respect to each other after the fibrin sealant product is cut.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

Figure 1:
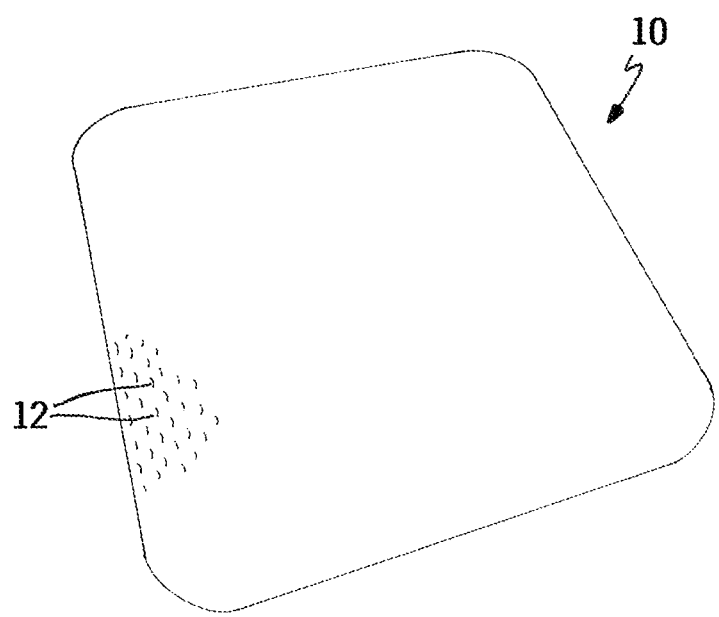
FIG. 1 is a perspective view of a fibrin sealant product according to an embodiment of the invention.
Figure 2:
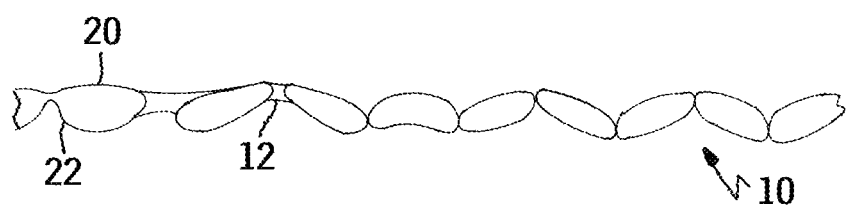
FIG. 2 is a sectional view of the fibrin sealant product.

An embodiment of the invention is directed to a system for providing hemostasis in a person or animal such as using a fibrin sealant product set forth in FIGS. 1 and 2. When the fibrin sealant product is applied to the injury site, the materials used to fabricate the fibrin sealant product dissolve to thereby release the materials to the injury site and provide the hemostatic effect or to seal a cerebral spinal fluid leak. Another embodiment of the invention is directed to the use of the fibrin sealant product for sealing a wound from which cerebral spinal fluid is leaking.

As described in more detail herein, the fibrin sealant product is particularly suited for the person who intends to use the fibrin sealant product to readily cut the fibrin sealant product into a shape that is particularly suited for a location at which the fibrin sealant product is intended to be used.

In some embodiments of the invention, only electrospun dextran fibers are utilized and thus after clot formation, there is no need to disturb the clot to remove fibrin sealant product components, since none remain at the site. The fibrin sealant product thereby does not leave any residual foreign bodies that elicit foreign body reactions or act as a nidus for infection. Furthermore, the fibrin sealant product does not contain any xenoproteins, which have the potential of eliciting immune reactions in persons on which the fibrin sealant product is used.

In other embodiments, as described below, the fibrin sealant product may include other materials such as support or backing material, which, after initial rapid application of the fibrin sealant product, may later be removed for further treatment of the wound by conventional methods.

The system generally includes a fibrin sealant product having a base to which at least one fibrin sealant agent is associated. In certain embodiments, the base is fabricated from electrospun dextran and the fibrin sealant agent is thrombin and/or fibrinogen.

Electrospinning is a processing strategy and can be scaled to accommodate the large volumes necessary to meet the needs of commercial processing. Additional details on the electrospinning process are provided in U.S. application Ser. No. 12/937,322, the contents of which are incorporated herein by reference.

In certain embodiments, the base used in the fibrin sealant product is formed of substantially homogeneous spun dextran. The amount of dextran used in each fibrin sealant product can vary depending on the size of fibrin sealant product that is being manufactured, with typical fibrin sealant product formulations using up to about 5 grams of dextran (usually 100,000-200,000 Mr) per fibrin sealant product. In other embodiments, the weight of dextran in each fibrin sealant product is between about 0.2 grams and about 2 grams.

Of more consequence is the concentration of dextran in the solution from which the fibers are electrospun. Generally, a solution of dextran for electrospinning will be of a concentration in the range of between about 0.1 and about 10 grams per milliliters of solvent. In other embodiments, the dextran concentration is between about 0.5 and about 5 grams per milliliter. In still other embodiments, the dextran is provided at a concentration of between about 1.2 grams to about 1.5 grams per milliliter of solution that is to be spun.

Those of skill in the art will recognize that a variety of liquid solvents exist in which it is possible to dissolve dextran. However, superior results for electrospinning dextran are generally achieved when the solvent is water, especially deionized or distilled or deionized, distilled (ddH20) or other forms of relatively pure water. In addition, there are no negative interactions during use of the fibrin sealant product associated with water remaining in the fibrin sealant product and there is far less environmental impact associated with the use of water as compared to many other solvents.

Depending on the intended use of the fibrin sealant product, care must be taken to ensure that the water is relatively free of microbes and other pathogens. Minimizing the presence of microbes in the water not only reduces the sterilization conditions but also avoids potential issues associated with endotoxins. Issues relating to the purity of the water are even more important when the product is intended to come into contact with cerebral spinal fluid.

The area (length and width) of the fibrin sealant product of the invention can vary widely and can be adjusted by adjusting spinning parameters. In addition, the mats of dextran fibers can be cut to a desired size after spinning. Generally, the fibrin sealant product will be from about 0.5 centimeters or less to about 30 centimeters or more in length and/or width, but larger or smaller sizes are also contemplated.

The thrombin and/or fibrinogen that are associated with the fibrin sealant product are in forms that are biologically active when they come into contact with blood. Hence, upon dissolution, the thrombin acts on the fibrinogen, converting it to fibrin, which then forms a clot within the wound to thereby staunch the flow of blood.

The fibrin sealant product is also particularly suited for stopping the flow of cerebral spinal fluid from a wound in the dura of the spine. It is believed that the mode of action may be different than the mode of action associated with the use of the fibrin sealant product for achieving hemostasis. In certain embodiments, the use of the fibrin sealant product to stop the flow of cerebral spinal fluid may be more of a mechanical process that is similar to the application of an adhesive instead of the coagulation cascade that is exhibited with hemostasis.

In certain embodiments, the thrombin and fibrinogen may be derived from human sources. In other embodiments, the thrombin and fibrinogen are salmon thrombin and fibrinogen.

The components used in fabricating the fibrin sealant product should be selected to be the same as components found in a living body where the fibrin sealant product is to be used. Alternatively, the components used in fabricating the fibrin sealant product are compatible with and readily broken down when the fibrin sealant product is used on or in a living body.

Using such a process minimizes complications associated with components of the fibrin sealant product not being promptly broken down as such a process could cause inflammation in the living body. Substantially, the only thing that remains after the use of the fibrin sealant product is the clot, which most living bodies are adapted to degrade over time.

In certain embodiments, a fibrinogen mixture is prepared by mixing fibrinogen with at least one salt. Mixing the fibrinogen with the at least one salt enhances the stability of the fibrinogen during storage prior to fabricating the fibrin sealant product as well as after the fibrin sealant product is fabricated. It is also possible to use stabilizing excipients such as albumin.

In certain embodiments, the fibrinogen mixture comprises fibrinogen that is derived from a human source. The fibrinogen may be provided in the fibrinogen mixture at a concentration of between about 40 percent by weight and about 70 percent by weight. In other embodiments, the fibrinogen is provided in the fibrinogen mixture at a concentration of between about 50 percent by weight and about 60 percent by weight.

In certain embodiments, the at least one salt is sodium chloride. The at least one salt is provided in the fibrinogen mixture at a concentration of between about 15 percent by weight and about 50 percent by weight. In other embodiments, the at least one salt is provided in the fibrinogen mixture at a concentration of between about 25 percent by weight and about 35 percent by weight.

The at least one salt may also include trisodium citrate that is provided in the fibrinogen mixture at a concentration of between about 10 percent by weight and about 30 percent by weight. In other embodiments, the trisodium citrate is provided in the fibrinogen mixture at a concentration of between about 15 percent by weight and about 25 percent by weight.

In other embodiments, the fibrinogen may be encapsulated with an encapsulating material that enhances the stability of the fibrinogen when stored either before or after fabricating the fibrin sealant product. An example of one encapsulating material is dextran. An example of one technique that may be used for encapsulating the fibrinogen is electrospinning using a multi-nozzle electrospinning system in which the fibrinogen is ejected from a first nozzle and the encapsulating material is ejected from a second nozzle.

In certain embodiments, a thrombin mixture is prepared by mixing thrombin with at least one salt and at least one buffer. Mixing the thrombin with the at least one salt and the at least one buffer enhances the stability of the thrombin prior to fabricating the fibrin sealant product as well as after the fibrin sealant product is fabricated.

In certain embodiments, the thrombin comprises thrombin that is derived from a human source. The thrombin may be provided in the thrombin mixture at a concentration of between about 0.5 percent by weight and about 2.5 percent by weight. In other embodiments, the thrombin is provided in the thrombin mixture at a concentration of between about 1.0 percent by weight and about 1.5 percent by weight.

In certain embodiments, the at least one salt is sodium chloride. The at least one salt is provided in the thrombin mixture at a concentration of between about 50 percent by weight and about 70 percent by weight. In other embodiments, the at least one salt is provided in the thrombin mixture at a concentration of between about 60 percent by weight and about 65 percent by weight.

In certain embodiments, the at least one buffer is bis(2-hydroxyethyl)-tris(hydroxymethyl)methane. The at least one buffer is provided in the thrombin mixture at a concentration of between about 15 percent by weight and about 35 percent by weight. In other embodiments, the at least one buffer is provided in the thrombin mixture at a concentration of between about 25 percent by weight and about 35 percent by weight.

The thrombin mixture may also include a biologically tolerable polymer. An example of one such biologically tolerable polymer is poly(ethylene glycol). The poly(ethylene glycol) may have a molecular weight of between about 5,000 and about 20,000. In certain embodiments, the poly(ethylene glycol) has a molecular weight of between about 7,000 and about 10,000.

The biologically tolerable polymer is provided in the thrombin mixture at a concentration of between about 5 percent by weight and about 25 percent by weight. In other embodiments, the biologically tolerable polymer is provided in the thrombin mixture at a concentration of between about 8 percent by weight and about 20 percent by weight. In still other embodiments, the concentration of the biologically tolerable polymer in the thrombin mixture is between about 13 percent by weight and about 20 percent by weight.

The components used to fabricate the thrombin mixture are mixed together until a substantially homogeneous mixture is prepared. The mixing process should be sufficiently gentle so that undue stress is not placed on the thrombin particles as such stress could impact the efficacy of the thrombin during the use of the fibrin sealant product.

In other embodiments, the thrombin may be encapsulated with an encapsulating material that enhances the stability of the thrombin when stored either before or after fabricating the fibrin sealant product. An example of one encapsulating material is dextran. An example of one technique that may be used for encapsulating the thrombin is electrospinning using a multi-nozzle electrospinning system in which the thrombin is ejected from a first nozzle and the encapsulating material is ejected from a second nozzle.

One of the aspects of obtaining enhanced efficacy of the fibrin sealant product is preparing a substantially homogeneous fibrin sealant mixture prior to applying the fibrin sealant mixture to the support material such as electrospun dextran while at the same time minimizing damage to the proteins used in the fibrin sealant mixture.

An important aspect of preparing the substantially homogeneous fibrin sealant mixture is ensuring that the proteins used in fabricating the fibrin sealant mixture do not form into large clumps because such clumps generate uneven concentrations of the proteins. One technique that has been found to be effective in preventing the formation of large clumps while minimizing damage to the proteins is by passing the components that are used in fabricating the fibrin sealant mixture through a sifter. In certain embodiments, the sifter is an automatic or a manual sifter having a mesh opening size of between about 0.2 millimeters and about 2.0 millimeters. In other embodiments, the sifter has a mesh opening size of between about 0.25 millimeters and about 0.75 millimeters. Such sifters may incorporate a cylindrical screen and the materials are urged against the screen using centrifugal motion.

Thereafter, the sifted materials are placed into a mixer. The mixer, the mixing conditions and the mixing duration should be selected to substantially homogeneously mix the components in the fibrin sealant mixture. In certain embodiments, the mixer utilizes multiaxial movement such as rotating and pivoting of the vessel in which the components are placed. The rate at which the mixer moves is selected to be sufficiently fast to cause mixing of the components while minimizing damage to the proteins during the mixing process.

The mixing can be performed for an extended period of time to ensure that the fibrin sealant mixture is substantially homogeneous. The mixing may be done for more than 60 minutes. In certain embodiments, the mixing is done for between about 120 and about 240 minutes.

Once the mixing of the fibrin sealant mixture has been completed, the fibrin sealant mixture may be packaged prior to using the fibrin sealant mixture in fabricating the fibrin sealant product. Packaging reduces the exposure of the fibrin sealant product to moisture as exposure to moisture can negatively impact the efficacy of the fibrin sealant mixture by causing the proteins to activate before the proteins are needed to achieve hemostasis.

To reduce the moisture concentration in the fibrin sealant mixture container, a desiccant may be placed in the fibrin sealant mixture container. A person of skill in the art will appreciate that a variety of desiccants may be selected based upon factors such as the initial moisture content of the fibrin sealant mixture.

The fibrin sealant mixture needs to be sterilized. Depending on the process that is used to fabricate the fibrin sealant product, sterilization can be done after the fibrin sealant mixture is packaged or after the fibrin sealant product is formed by applying the fibrin sealant mixture to the support material.

A variety of techniques may be used to sterilize the fibrin sealant mixture. The selected sterilization technique should minimize denaturation of the proteins. Even while the denaturation of the proteins is minimized, it is anticipated that at least some of the proteins will be denatured during the sterilization process.

The moisture level in the fibrin sealant mixture container can further be reduced by injecting an inert gas into the container. In certain embodiments, the inert gas is nitrogen. The processing reduces the moisture level in the fibrin sealant mixture container to less than about 6 percent, which is a significant reduction from the initial moisture level of the fibrin sealant mixture, which is about 11 percent depending on ambient conditions. In other embodiments, the moisture level in the fibrin sealant mixture container is less than about 3 percent. Another benefit of the nitrogen injection is that the nitrogen injection displaces oxygen from the container.

Another technique to minimize denaturation of the proteins in the fibrin sealant mixture is to maintain the fibrin sealant mixture at a low temperature prior to use. The temperature may be less than about 46° F. In other embodiments, the temperature is less than about 0° F. One technique that may be used to maintain the fibrin sealant mixture and/or the fibrin sealant product at the low temperature is placing dry ice adjacent to the fibrin sealant mixture and/or the fibrin sealant product.

The quantity of fibrinogen added to the fibrin sealant product may be adjusted by changing either the concentration of the fibrinogen in the fibrin sealant mixture or changing the rate at which the fibrin sealant mixture is used in the fibrin sealant product. The quantity of fibrinogen added to the fibrin sealant product is generally in the range of from about 10 milligrams to about 3 grams. In certain embodiments, the amount of fibrinogen in each of the fibrin sealant products is between about 20 milligrams to about 1 gram.

The quantity of thrombin added to the fibrin sealant product may be adjusted by changing either the concentration of the thrombin in the fibrin sealant mixture or changing the rate at which the fibrin sealant mixture is used in the fibrin sealant product. The quantity of thrombin added to each of the fibrin sealant products is generally between about 10 and 10,000 NIH Units. In certain embodiments, the amount of thrombin in each of the fibrin sealant products is between about 20 and 6,000 NIH Units.

An important aspect of preparing the fibrin sealant product is ensuring that the fibrin sealant mixture is not deposited on the electrospun dextran into large clumps because such clumps generate uneven concentrations of the proteins. In certain embodiments, a screen may be used to deposit the fibrin sealant mixture in a substantially uniform fashion across the entire electrospun dextran sheet. Such a process is important with respect to uniformity of the final fibrin sealant product because gaps would compromise the ability to reduce flow of the blood and/or cerebral spinal fluid.

In some embodiments, the therapeutic agents may themselves be electrospun. For example, the therapeutic agents are dissolved in and spun from a solution. In some embodiments, the therapeutic agents may be electrospun into fibers. In other embodiments, the active agents may be electrospun into other forms such as droplets, beads, etc.

In some applications, active agents such as thrombin may be electrosprayed with sucrose to form sugar droplets, which tends to stabilize thrombin and can also "trap" other substances of interest for delivery to the fibrin sealant product.

For thrombin and fibrinogen, in most embodiments, these (or other) active agents are in a finely dispersed dry, particulate or granular form e.g. as a fine powder or dust, as electrospinning may tend to decrease their activity. In other words, the active agents are not electrospun either by themselves.

Usually the agents are bioactive agents that have a beneficial or therapeutic effect at the wound site. In one embodiment, the site is a bleeding wound at which it is desired to form a blood clot to stop or slow the bleeding. In this embodiment, the therapeutic substances of interest may include, for example, thrombin and fibrinogen, although other agents active in promoting hemostasis may also be included.

In addition, electrospun or non-electrospun collagen, agents that absorb water, various dry salts that would tend to absorb fluids when placed in contact with e.g. blood; engineered thrombin or thrombin mimics; engineered fibrinogen; agents that cause vasospasm (e.g. ADP, 5-hydroxytryptamine, 5-HT and thromboxane (TXA-2)) to help contract and seal a bleeding vessel, etc. may also be included.

Other components of the clotting cascade may be added to the fibrin sealant product, for example: tissue factors that are normally only expressed on the surface of damaged cells and that start the normal clotting cascade; serotonin which enhances platelet clumping and promotes vessel constriction; and other agents that are used to replace missing components of the clotting cascade in hemophilia, for example, factor 7 (which activates the so called external extrinsic coagulation cascade) and crude extracts of platelets.

Active agents that function to promote late stages of wound healing may also be included to, for example, facilitate cell migration and remodeling. The incorporation of collagen is an example of such an active agent.

One or more of any of these active agents may be used in the practice of the present invention. The therapeutic agents must be amenable to drying and are associated with the other components of the fibrin sealant product in the dry state, since liquid may negatively affect at least one of the components used in the fibrin sealant product. For example, the active agents may be desiccated or lyophilized, or water may be removed by other means.

Association of substances of interest with the electrospun dextran base may be accomplished by any of many suitable techniques that are known to those of skill in the art, and will depend in part on the precise form of the substance and the means at hand. For example, for powdered, particulate thrombin and fibrinogen, association may be carried out by sprinkling, shaking, blowing, etc. the agents onto a layer of the excipient or carrier.

In certain embodiments, the electrospun dextran base is placed on a vacuum table, which not only retains the electrospun dextran base in a substantially stationary position during the fabrication process but also causes the fibrin sealant agents to be drawn into the electrospun dextran base. This process thereby reduces the potential of the fibrin sealant agent becoming disassociated from the electrospun dextran base while stored in a package as well as when removed from the package prior to applying to the wound.

Depending on the density of the fiber mat, the substances of interest may become relatively evenly dispersed throughout the woven mat of fibers or may be largely confined to the topmost section of the fiber mat. If no backing is present, the latter embodiment is preferable to prevent the particulate substance of interest from falling through and out of the mat.

The association of substances of interest with the electrospun dextran base may be carried out according to many different arrangements. For example, a first layer of electrospun dextran may be formed, and one or more of the substances may be associated with the first layer. Then another second layer of electrospun dextran may be formed on top of the substance(s) of interest, and the same or other substances of interest may be associated with the second layer, and so on.

A final or outermost layer of electrospun dextran may be added to prevent the dislodgement of substances of interest from the layer(s) below. The number of layers of excipient that are used in the fibrin sealant product of the invention may vary widely, from as few as 1-2 to as many as several dozen, or even several hundred, depending on the desired characteristics of the fibrin sealant product.

Typically, a fibrin sealant product will contain 1-2 layers. In other embodiments, the fibrin sealant product may include between 2-20 layers. The very slight amount of moisture that is present in a prepared fibrin sealant product may help to trap and retain the thrombin and fibrinogen on the surface of the fibrin sealant product.

The fibrin sealant product may be formed in a variety of sizes depending on the intended use of the fibrin sealant product. In certain embodiments, a surface area of the fibrin sealant product is less than about 400 square centimeters. In other embodiments, the surface area of the fibrin sealant product is between about 1 square centimeter and about 100 square centimeters.

In certain embodiments, the fibrin sealant product has a generally square shape. A person of skill in the art will appreciate that the fibrin sealant product may be fabricated in a variety of alternative shapes, examples of which include rectangular, circular and oval. When the fibrin sealant product is formed with a generally square shape, corners of the fibrin sealant product may be curved as illustrated in FIG. 1.

The layers are joined together using a crimping process in which the crimps 12 are dispersed over the surface of the fibrin sealant product 10. Each of the crimps 12 occupies a relatively small amount of the surface area of the fibrin sealant product 10. The crimps 12 are placed in a spaced-apart configuration on the surface of the fibrin sealant product 10. The crimps 12 thereby hold together an upper layer 20 and a lower layer 22 of the fibrin sealant product 10.

The crimps 12 may be formed in a variety of shapes using the concepts of the invention. In certain embodiments, the crimps 12 may have a pyramidal shape that is defined by four sides as illustrated in FIG. 1. In other embodiments, the crimps 12 may have a conical shape.

In certain embodiments, at least a portion of the crimps 12 may be aligned in rows and columns. To minimize the potential of the person using the crimps 12 as guides when cutting the fibrin sealant product, the rows and columns of crimps 12 may be oriented at an angle with respect to at least one of the edges of the fibrin sealant product. In certain embodiments, the rows and columns of crimps 12 are oriented at an angle of about 45 degrees with respect to at least one of the edges of the fibrin sealant product as illustrated in FIG. 1. In such a configuration, the crimps 12 would typically not be aligned along various shapes in which the person using the fibrin sealant product 10 would likely cut.

In other embodiments, the crimps 12 may be randomly placed on the fibrin sealant product 10. As used herein, randomly placing the crimps 12 on the fibrin sealant product 10 means that the crimps 12 are not generally aligned along a straight line, a curved line or a geometric shape when viewed from the perspective of a medical professional who is using the fibrin sealant product 10.

Whether the crimps 12 are placed in a particular pattern or a random configuration, the crimps 12 should be dispersed in a relatively even manner over the surface of the fibrin sealant product 10 to generally maintain the fibrin sealant agents in a dispersed configuration in the fibrin sealant product 10 and substantially prevent the fibrin sealant agents from being disassociated from the fibrin sealant product 10.

The crimps 12 thereby cause the fibrin sealant agents to be maintained in a substantially stationary position on the fibrin sealant product 10. The crimps 12 thereby substantially prevent the fibrin sealant agent from becoming disassociated from the fibrin sealant product 10 such as by falling off of the fibrin sealant product 10.

While it is possible for the fibrin sealant agent that is proximate the edges of the fibrin sealant product 10 to become disassociated from the fibrin sealant product 10 because the edge is not sealed, the placement of the crimps 12 over the surface of the fibrin sealant product 10 and the dispersal of the fibrin sealant agents minimizes the loss of the fibrin sealant agent during the handling of the fibrin sealant product 10.

As used herein, relatively evenly dispersing the crimps 12 on the surface of the fibrin sealant product 10 means that a difference between the number of crimps 12 in a specified area of the fibrin sealant product 10 is less than about 30 percent. In other embodiments, the difference between the number of crimps 12 in the specified area of the fibrin sealant is less than about 20 percent.

To minimize the fibrin sealant agents becoming disassociated from the fibrin sealant product 10 or avoid the layers becoming separated from each other or moving with respect to each other, a relatively large number of crimps 12 are placed on the surface area of the fibrin sealant product 10. In certain embodiments, there are at least about 10 crimps 12 per square centimeter on the surface of the fibrin sealant product 10. In other embodiments, there are between about 15 and 25 crimps 12 per square centimeter on the surface of the fibrin sealant product 10. In certain embodiments, the number of crimps 12 in each square centimeter region may be approximately equal.

A variety of techniques may be used to form the crimps 12 on the fibrin sealant product 10. In certain embodiments, the fibrin sealant product 10 is placed on a generally flat support surface and a crimping device engages a surface of the fibrin sealant product 10 that is opposite the support surface. In other embodiments, crimping devices engage opposite surfaces of the fibrin sealant product 10.

The force applied to the fibrin sealant product 10 by the crimping device should be sufficient to urge the electrospun dextran layers 20, 22 into engagement with each other so that the electrospun dextran layers resist separation when the fibrin sealant product 10 is stored prior to use, when the fibrin sealant product 10 is cut into a desired shape and when the fibrin sealant product 10 is applied to a location where it is desired to achieve hemostasis. In certain embodiments, the crimping process may cause elevated pressure and/or temperature along the crimping surface to an extent such that the electrospun fibers in the fibrin sealant product 10 melt or fuse together. Such a process enhances the strength of the bond between the layers 20, 22.

In certain situations, it is desired to cut the fibrin sealant product 10 so that the fibrin sealant dressing 10 has an appropriate shape or size for the region in which hemostasis is needed. In prior configurations such as described in Olson, U.S. Patent Publication No. 2016/0038627, the layers were crimped around the edge thereof but this edge crimping did not retain the layers in a stationary position with respect to each other or prevent the fibrin sealant agent from being disassociated from the fibrin sealant product when the fibrin sealant product 10 is cut.

An important aspect of the invention is that the fibrin sealant product 10 does not have any guides caused by the crimping that encourage or suggest a person using the fibrin sealant product 10 to cut the fibrin sealant product in particular shape(s) or size(s). Without such guides, the person using the fibrin sealant product 10 may envision cutting the fibrin sealant product 10 into a shape and size that is particularly suited for the region in which the fibrin sealant product 10 is intended to be applied to achieve hemostasis. Such a process minimizes the presence of excess fibrin sealant product 10 at the use location. In other embodiments, the fibrin sealant product 10 may include at least one guide to facilitate accurately cutting the fibrin sealant product 10 in particular shapes. For example, the guide may be useful when cutting the fibrin sealant product 10 into a relatively long and narrow shape.

The nature of the fibrin sealant product 10 allows the person using the fibrin sealant product 10 to shape the fibrin sealant product 10 using tools that are typically available in a medical setting such as an operating room. An example of one such tool that may be used to shape the fibrin sealant product 10 is scissors.

The fibrin sealant product 10 is thereby suited for customization for use in highly disparate settings such as a small circle or square shape for incidental durotomies in the spine as well as a large horseshoe, ellipses or other irregular shape when used in conjunction with cranial durotomies. The invention also facilitates the person cutting the fibrin sealant product 10 to round the corners so that the fibrin sealant product 10 generally conforms to the rounded corners that naturally occur in craniotomies.

The relative thinness of the fibrin sealant product 10 and the nature in which the layers are joined together provide the fibrin sealant product 10 with a high degree of flexibility, which enhances the ability of the fibrin sealant product 10 to bend to conform to the surface on which it is desired to achieve hemostasis. Such enhanced conformability of the fibrin sealant product 10 enhances the ability of the fibrin sealant product 10 to achieve hemostasis, which decreases the volume of blood lost by the patient, which enhances the prognosis for the patient to make a full recovery. Similar results may be attained from the use of the fibrin sealant product 10 to stop the loss of cerebral spinal fluid.

For example, when the fibrin sealant product 10 is used in conjunction with spinal cord durotomies, the flexibility of the fibrin sealant product 10 enables the fibrin sealant product 10 to conform to the generally cylindrical shape of the spinal cord while at the same time minimizing pressure that is exerted on the spinal cord during the process of positioning the fibrin sealant product 10 with respect to the durotomy until hemostasis is achieved. Additionally, the flexible nature of the fibrin sealant product 10 provides the fibrin sealant product 10 with a very good ability to conform to the generally spherical shape of certain parts of the brain.

This process causes the layers to resist separation or movement with respect to each other, which enhances the ability to accurately apply the fibrin sealant product 10 to a location where hemostasis is desired. This process also causes the fibrin sealant agents to be trapped between the layers. The trapping of the fibrin sealant agents not only prevents the fibrin sealant agents from becoming dislodged from the fibrin sealant product 10 but also causes the fibrin sealant agents to substantially remain in the dispersed configuration in the fibrin sealant product 10. This process thereby enhances the ability of the fibrin sealant product 10 to achieve hemostasis.

The height or thickness of the fibrin sealant product 10 can vary considerably depending on the intended use of the fibrin sealant product 10. In certain embodiments, the fibrin sealant product 10 has a height of between about 1 millimeter and about 5 centimeters.

The thickness of the fibrin sealant product 10 (which is related to the volume) may impact the rate of dissolution of the dextran upon contact with liquid. For example, a thin fibrin sealant product 10 (e.g. about 2 millimeters) will dissolve more rapidly than a fibrin sealant product 10 that is thicker, providing the loft of the fibers is comparable.

In most embodiments, dissolution of the dextran fibers is extremely rapid, e.g. about 5 minutes or less after exposure to liquid, or about 4 minutes or less, or about 3 minutes or less, or about 2 minutes or less, or about 1 minute or less. In certain embodiments, the fibrin sealant product 10 substantially dissolves in between about 1 second and about 20 seconds.

This rapid dissolution may be referred to herein as "instantaneous" or "immediate" dissolution. Compression of an electrospun dextran mat may be used to modulate the rate of dissolution.

The rapid rate of dissolution is advantageous, particularly when delivering biologically active agents (e.g. fibrin sealant agents) to a site of action such as a wound. Rapid dissolution of the carrier dextran fibers provides extremely rapid delivery of the fibrin sealant agents to the wound upon deployment of the fibrin sealant product 10.

Generally, the amount of water that is present in the substances when they are associated with the electrospun dextran fibers is less than about 5%, and preferably less than about 2%. These substances retain full or partial activity when rehydrated, e.g. in blood or cerebral spinal fluid. Generally, therapeutic substances associated with the fibrin sealant product 10 of the invention retain, upon contact with liquid, at least about 25%, or about 50%, or even about 75% to 100% of their activity before drying or desiccation, as compared to standard preparations of the substance using standard assays that are known to those of skill in the art.

If thrombin is included in the fibrin sealant product 10, it may be desirable to reduce the moisture content of the fibrin sealant product 10 (e.g. a bandage or gauze) to less than about 5% to preserve thrombin activity during sterilization.

This moisture content reduction can be achieved by drying the fabricated fibrin sealant product 10, e.g., under a vacuum, or by using a fabrication method that reduces moisture content from the beginning.

The fibrin sealant product 10 may include one or more stabilizers such as is described in U.S. application Ser. No. 13/622,690, which is assigned to the assignee of the present application and the contents of which are incorporated herein by reference. The stabilizers may enhance the ability of the fibrin sealant product 10 to dissolve when the fibrin sealant product 10 is applied to the injury site.

Prior to use of the fibrin sealant product 10, it may be desirable for the fibrin sealant product 10 to be carried by a person on whom the fibrin sealant product 10 could potentially be used and/or by a person who could potentially use the fibrin sealant product 10. In other embodiments, the fibrin sealant product 10 resists degradation at temperatures of more than 140° F. to less than 0° F.

In certain embodiments, the fibrin sealant product 10 should resist degradation when exposed to the elevated temperature such as up to about 150° F. for more than about 3 hours. In other embodiments, the fibrin sealant product 10 should resist degradation when exposed to the elevated temperature for up to about 24 hours.

A threshold for the fibrin sealant product 10 to be viewed as not experiencing degradation is that the fibrin sealant product 10 does not exhibit noticeable visible physical changes when viewing the fibrin sealant product 10 without magnification. The fibrin sealant product 10 should also not experience noticeable physical changes when the fibrin sealant product 10 is examined with magnification such as with a magnifying glass or a microscope.

The preceding characteristics should be displayed by the fibrin sealant product 10 regardless of whether the fibrin sealant product 10 is retained in the packaging materials while exposed to the elevated temperature conditions.

The stabilizer also enhances the usable shelf life of the fibrin sealant product 10. In certain embodiments, the stabilizer provides the fibrin sealant product 10 with a shelf life of at least about 2 years. In other embodiments, the fibrin sealant product 10 exhibits a shelf life of at least 3 years. As used herein, the term usable shelf life means that the fibrin sealant product 10 does not exhibit noticeable degradation when viewed without magnification or with magnification such as a magnifying glass or microscope, and does not exhibit excessive denaturation of the proteins.

To minimize the potential of degradation of the fibrin sealant product 10, the fibrin sealant product 10 should be protected from exposure to moisture because when the components used in the fibrin sealant product 10 are exposed to moisture, the components degrade such as by dissolving.

In some embodiments of the invention, the fibrin sealant products 10 also include one or more support structures or support materials incorporated therein. For example, a backing may be incorporated into the fibrin sealant product 10.

The support material may be formed from various electrospun materials such as polyglycolic acid (PGA), polylactic acid (PLA), and their copolymers (PLGAs); charged nylon, etc. In one embodiment, the support material is compressed electrospun dextran fibers. By "compressed electrospun dextran fibers," it is meant that electrospun dextran fibers are compressed together under pressure.

The support material may or may not be soluble in liquid, or may be slowly soluble in liquid, and may or may not be permeable to liquid. Slowly soluble materials include those from which absorbable or dissolving (biodegradable) stitches or sutures are formed, including PGA, polylactic and caprolactone polymers.

In certain embodiments, the support material may dissolve relatively quickly such as less than about 1 hour. In other embodiments, the support material may dissolve in a short, but not too short time, such as within about a few seconds, in order that the proteins may be quickly delivered through a wet area, thereby reaching their intended target. In other embodiments, the support material may dissolve within from about 10 days to 8 weeks. In either case, the support material provides the advantage of not having to remove the fibrin sealant product and risk disrupting the clot.

However, in any case, the support material should not interfere with the immediate dissolution of the fibrin sealant product and delivery of the active agents associated therewith into the liquid that dissolves the fibrin sealant product. All such arrangements, shapes, and embodiments of carrier layers and support materials as described herein are intended to be encompassed by the invention.

The fibrin sealant product 10 may be sterilized prior to use, generally by using electromagnetic radiation, for example, X-rays, gamma rays, ultraviolet light, etc. Typically, the fibrin sealant product is sterilized using X-rays in a dose of about 5 kilograys (kGray). Any method that does not destroy the carrier or the activity of substances associated with the fibers may be used to sterilize the fibrin sealant product 10 of the invention.

The fibrin sealant product 10 may also include diagnostic agents that can be used by the treating medical professional to diagnose the nature of the injury. In certain embodiments, the diagnostic agent may change colors to indicate the presence of particular chemicals in the blood or to indicate particular characteristics of the blood. For example, if the patient is currently taking medications that cause thinning of the patient's blood. The diagnostic agents could also change colors to indicate the oxygen and/or glucose level of the blood.

In other embodiments, the product of the invention need not comprise agents that promote clotting at all. Those of skill in the art will recognize that the product of the invention is highly suitable for delivering many substances of interest to a desired liquid environment or location. For example, the product may be designed for delivery of therapeutic or beneficial substances to any moist environment of the body, where there is sufficient liquid to dissolve the electrospun dextran fibers and release the active substance, and where dissolved dextran is not problematic.

Such substances may include, for example, enzymes or their precursors (e.g. pro-enzymes or zymogens) and their substrates, substances that activate a protein or enzyme (e.g. proteases, cofactors, etc.), and the like.

For example, fibrin sealant products 10 comprised of only thrombin might be used for small injuries or in combination with other interventions. In addition, other therapeutically beneficial substances may also be associated with the fibrin sealant product 10, including but not limited to: antibiotics, antiviral agents, anti-helminthic agents, anti-fungal agents, medicaments that alleviate pain, growth factors, bone morphogenic protein, vasoactive materials (e.g. substances that cause vasospasms), steroids to reduce inflammation, chemotherapy agents, contraceptives, etc.

Examples include but are not limited to oral, nasal, tracheal, anal, lung, and vaginal delivery of substances such as anti-microbial agents, analgesic agents, nutritional agents, etc. Oral applications include the delivery of substances useful for dental treatments, e.g. antibiotics, pain medications, whitening agents, etc.

In some embodiments, no bodily fluid is present (or if insufficient body fluid is present) and the applied fibrin sealant product can be "activated" by wetting, e.g. by spraying, or by otherwise applying a source of moisture (e.g. by exposing the fibrin sealant product to a moist material such as a sponge), or immersing the fibrin sealant products 10 into a liquid (e.g. a body of water), to cause release of the agents of interest associated with the dextran fibers.

In addition to being used to produce hemostasis in humans, the concepts of the invention may be adapted for use in conjunction with other animals. Examples of such animals on which the invention can be used include dogs and cats.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A fibrin sealant product comprising:
   a plurality of layers that each comprise:
   a dextran support; and
   at least one fibrin sealant agent placed on the dextran support, wherein the plurality of layers are placed in a stacked configuration to form the fibrin sealant product and wherein the fibrin sealant product has an edge; and
   a plurality of crimps dispersed over a surface of the fibrin sealant product to retain the plurality of layers in a stationary position with respect to each other, wherein at least a portion of the plurality of crimps are arranged in a plurality of rows and columns and wherein the rows and columns are not parallel or perpendicular to the edge.

2. The fibrin sealant product of claim 1, wherein the plurality of crimps retains the at least one fibrin sealant agent in a substantially stationary position with respect to the dextran support.

3. The fibrin sealant product of claim 1, wherein the plurality of crimps are dispersed substantially evenly over a surface of the fibrin sealant product.

4. The fibrin sealant product of claim 1, wherein there are between about 5 and 25 crimps per square centimeter on the fibrin sealant product.

5. The fibrin sealant product of claim 1, wherein the rows and columns are oriented at an angle with respect to the edge of about 45 degrees.

6. The fibrin sealant product of claim 1, wherein the dextran support comprises electrospun dextran.

7. The fibrin sealant product of claim 1, wherein the at least one fibrin sealant agent comprises at least one of thrombin and fibrinogen.

8. A method of preparing a fibrin sealant product comprising:
   fabricating a plurality of layers that each comprise:
   forming a dextran support; and
   dispensing at least one fibrin sealant agent on the dextran support;
   arranging the layers in a stacked configuration to form the fibrin sealant product, wherein the fibrin sealant product has an edge; and
   applying a plurality of crimps to the fibrin sealant product to retain the plurality of layers in a stationary position with respect to each other, wherein the plurality of crimps are dispersed over a surface of the fibrin sealant product, wherein at least a portion of the plurality of crimps are arranged in a plurality of rows and columns and wherein the rows and columns are not parallel or perpendicular to the edge.

9. The method of claim 8, wherein the plurality of crimps retains the at least one fibrin sealant agent in a substantially stationary position with respect to the dextran support.

10. The method of claim 8, wherein the plurality of crimps are dispersed substantially evenly over a surface of the fibrin sealant product.

11. The method of claim 8, wherein the dextran support comprises electrospun dextran and wherein the at least one fibrin sealant agent comprises at least one of thrombin and fibrinogen.

12. A method of preparing a fibrin sealant product comprising:
   fabricating a plurality of layers that each comprise:
   forming a dextran support; and
   dispensing at least one fibrin sealant agent on the dextran support;
   arranging the layers in a stacked configuration to form the fibrin sealant product, wherein the fibrin sealant product has an edge;
   applying a plurality of crimps to the fibrin sealant product, wherein the plurality of crimps are dispersed over a surface of the fibrin sealant product, wherein at least a portion of the plurality of crimps are arranged in a plurality of rows and columns and wherein the rows and columns are not parallel or perpendicular to the edge;
   providing a location at which it is desired to use the fibrin sealant product to achieve hemostasis, wherein the location has a shape and a size; and
   cutting the fibrin sealant product to change at least one of a shape and a size of the fibrin sealant product, wherein cutting the fibrin sealant product provides the fibrin sealant product with the shape and the size that are similar to the shape and the size of the location where it is desired to use the fibrin sealant product, wherein the plurality of crimps retain the plurality of layers in a stationary position with respect to each other after the fibrin sealant product is cut and wherein the arranging of the portion of the plurality of crimps in the plurality of rows and columns that are not parallel or perpendicular to the edge causes the portion of the plurality of crimps to not act as a guide for the cutting of the fibrin sealant product.

13. The method of claim 12, wherein the plurality of crimps is substantially not arranged in a shape that is similar to the shape of the location at which the fibrin sealant product is used.

14. The method of claim 12, wherein the plurality of crimps retains the at least one fibrin sealant agent in a substantially stationary position with respect to the dextran support and wherein the plurality of crimps are dispersed substantially evenly over a surface of the fibrin sealant product.

15. The method of claim 12, wherein the dextran support comprises electrospun dextran and wherein the at least one fibrin sealant agent comprises at least one of thrombin and fibrinogen.

* * * * *